(12) United States Patent
Lopes

(10) Patent No.: US 9,615,899 B2
(45) Date of Patent: Apr. 11, 2017

(54) CONSTRUCTIVE SYSTEM OF A SELF-LIGATING BRACKET WITH VARIABLE RESISTANCE TO SLIDING

(71) Applicant: Alexandre Gallo Lopes, Ribeirão Preto (BR)

(72) Inventor: Alexandre Gallo Lopes, Ribeirão Preto (BR)

(*) Notice: Subject to any disclaimer, the term of this patent is extended or adjusted under 35 U.S.C. 154(b) by 25 days.

(21) Appl. No.: 14/151,619

(22) Filed: Jan. 9, 2014

(65) Prior Publication Data

US 2014/0199648 A1 Jul. 17, 2014

(30) Foreign Application Priority Data

Jan. 17, 2013 (BR) .......................... 10 2013 001208 4

(51) Int. Cl.
*A61C 7/28* (2006.01)
(52) U.S. Cl.
CPC ........ *A61C 7/287* (2013.01); *A61C 2201/007* (2013.01)
(58) Field of Classification Search
CPC .......... A61C 7/28; A61C 7/285; A61C 7/287; A61C 7/30; A61C 7/34; A61C 2201/007
USPC ...................................... 433/8–17
See application file for complete search history.

(56) References Cited

U.S. PATENT DOCUMENTS

| | | | | |
|---|---|---|---|---|
| 3,748,740 A | * | 7/1973 | Wildman | 433/11 |
| 4,149,314 A | * | 4/1979 | Nonnenmann | 433/13 |
| 4,547,153 A | * | 10/1985 | Taylor | 433/11 |
| 5,474,445 A | * | 12/1995 | Voudouris | 433/10 |
| 5,586,882 A | * | 12/1996 | Hanson | 433/13 |
| 5,857,850 A | * | 1/1999 | Voudouris | 433/11 |
| 5,908,293 A | * | 6/1999 | Voudouris | 433/10 |
| 5,913,680 A | * | 6/1999 | Voudouris | 433/10 |
| 6,071,118 A | * | 6/2000 | Damon | 433/9 |
| 6,247,923 B1 | * | 6/2001 | Vashi | 433/10 |
| 6,506,049 B2 | * | 1/2003 | Hanson | 433/11 |
| 6,582,226 B2 | * | 6/2003 | Jordan et al. | 433/10 |
| 7,963,768 B2 | * | 6/2011 | Hilliard | A61C 7/287 433/11 |
| 8,029,276 B1 | * | 10/2011 | Lokar | 433/10 |
| 8,282,392 B2 | * | 10/2012 | Hilliard | 433/11 |
| 8,414,292 B2 | | 4/2013 | Lopes | |
| 8,585,398 B2 | * | 11/2013 | Yeh et al. | 433/10 |
| 9,339,353 B2 | | 5/2016 | Voudouris | |
| 2010/0062387 A1 | * | 3/2010 | Hilliard | 433/11 |
| 2010/0105000 A1 | * | 4/2010 | Scommegna et al. | 433/10 |
| 2010/0112508 A1 | | 5/2010 | Lopes | |
| 2010/0151403 A1 | * | 6/2010 | Tuneberg et al. | 433/10 |

(Continued)

FOREIGN PATENT DOCUMENTS

BR DI6804372-4 F 10/2008
BR MU8802474-1 U2 7/2010

(Continued)

*Primary Examiner* — Cris L Rodriguez
*Assistant Examiner* — Hao D Mai
(74) *Attorney, Agent, or Firm* — Arent Fox LLP

(57) ABSTRACT

A self-ligating bracket and system with variable resistance to sliding. The bracket includes locking elements and/or deflection control components that govern the flexibility and movement of blades or clips that extend over an archwire slot, in order to adjust the action of such blades or clips relative to an archwire positioned within an archwire slot in the bracket.

7 Claims, 14 Drawing Sheets

(56) References Cited

U.S. PATENT DOCUMENTS

| | | | |
|---|---|---|---|
| 2010/0279247 A1* | 11/2010 | Kesling | 433/10 |
| 2011/0212407 A1* | 9/2011 | Hilliard | A61C 7/22 433/11 |
| 2011/0269093 A1* | 11/2011 | Waugh, Jr. | 433/10 |
| 2013/0045455 A1* | 2/2013 | Farzin-Nia | 433/11 |
| 2013/0224676 A1* | 8/2013 | Alauddin et al. | 433/3 |
| 2013/0260329 A1* | 10/2013 | Voudouris | 433/9 |
| 2014/0212828 A1* | 7/2014 | Falcone et al. | 433/11 |

FOREIGN PATENT DOCUMENTS

| | | |
|---|---|---|
| BR | MU8902352-8 U2 | 6/2011 |
| BR | 20 2012 002849-8 U2 | 3/2014 |

\* cited by examiner

CONSTRUCTIVE SYSTEM OF A SELF-LIGATING BRACKET WITH VARIABLE RESISTANCE TO SLIDING

BACKGROUND

This application claims priority to Brazilian Application No. 10 2013 001208 4 filed Jan. 17, 2013, the entire contents of which are incorporated herein by reference.

1. Field of the Invention

This patent application relates to an innovative constructive system of a self-ligating bracket with variable resistance to sliding, and, more specifically, a system in which by the inclusion of certain components in the structure of the bracket, either extending towards the archwire slot and/or laterally, distinct behavior of the clip or blade may be produced, and therefore in the interaction with the archwire, thereby enabling a variation in the resistance to sliding in the interface.

2. Background of the Technology

Orthodontic brackets are the main elements in a group of accessories that perform corrective action in the treatment to improve occlusion and dental positioning for the patient.

According to established orthodontic techniques of the related art, it is necessary to connect an archwire to the bracket using an elastomeric or metallic ligature tie.

In the case of brackets with tie wings (which may for example, include a pair of wings also interchangeably referred to herein as "twin wings"), the ligature must be tensioned so as to include the tie wings mesially and distally housing itself underneath the recess of the wings. This procedure, involves a selection between an elastomeric ligature or metallic ligature tie, the process being repetitive and time consuming for the professional.

Elastomeric ligature ties that securely retain the archwire inside the slot suffer degradation in the oral environment, hindering control over dental movement. This degradation causes friction and interactions of unwanted forces thereby preventing uniformity in the ligating process. Another negative point for the elastomeric ligature ties is that they accumulate organic material, allowing the formation of bacterial plaque and complicating oral hygiene.

On the other hand, metallic ligature ties, due to the vibratory forces of mastication, become loose with time, resulting in a loss of control and lack of uniformity in the ligating process. Metallic ligature ties also have sharp points, which cause them to be prone to harming the people involved and exposing professionals to infections by bacteria or viruses, such as Hepatitis B.

Therefore, in an orthodontic treatment, it is fundamental to exercise control of the forces involved in moving the arches and teeth, carried out by the conjunction of the elements involved, e.g., by the bracket, the locking mechanism and ligating the archwire, in combination with expertise from the professional involved.

In order to better illustrate the above statement, according to the characteristics of the forces of the archwires used in the beginning of treatment, an interaction of forces occurs when the archwires contact the blade or clip of the locking mechanism of the slot. During the interaction, depending on the amplitude of the movement, the arch may or may not energize the arms of the blade or clip. In this context, the force of the archwires applied at the beginning of treatment is lower, performing a function of dental movement that is more effective in a passive environment. In this situation the arms of the blade or clip should not deflect.

In the current state of the related art for this technique, some patent documents describe means of controlling the load friction and the interval of the blade or clip movement over the archwire. For example, US Patent Publ. No. 20100062387 deals with a clip for a self-ligating bracket with a projection between the labial surface of the bracket and the vestibular portion of the clip that can be turned in adjustment intervals. A screw stem or an eccentric action mechanism can be utilized as a fixation element.

The utilization of screws and other features and/or methods to limit the action range of the blade or clip leads to frequent manual adjustments, thereby undercutting one main advantage of a self-ligating bracket, e.g., that of enabling the performance of fast and easy clinical management procedures.

Other examples of such solutions are depicted in U.S. Pat. No. 6,257,883, which illustrates a constructive structure for the bracket configuration with a housing in the extremities of the clip or blade under the tie wings, enabling inhibiting of the labial displacement of the clip so as to dissipate the exceeding forces.

There remains an unmet need for a constructive system of a self-ligating bracket with variable resistance to sliding.

SUMMARY OF THE INVENTION

In accordance with aspects of the present invention, provided is constructive system of a self-ligating bracket with variable resistance to sliding based on a constructive alteration in the body of the bracket with the advance or retraction of the complements of sliding channel walls in a first and/or second set of tie wings towards the archwire slot or laterally in the mesial-distal direction, making it possible to increase or reduce the force over the clip or blade promoting a higher or lower flexibility of the ligating member, therefore enabling the variation of the resistance to sliding. In one variation, as the walls of the sliding channels approach the archwire slot, the resistance to sliding is increased. In testing cycles to verify the influence of the positioning of certain components in relation to the archwire slot (also interchangeably referred to herein as "deflection control components"), it has been found that, for every 0.01 mm of extension of such deflection control components towards the slot, an increase of 150-200 grams of force in the direction to deflect the blade or clip perpendicular to the archwire slot was recorded, therefore directly influencing the friction load transmitted by the blade or clip to the archwire.

In accordance with aspects of the constructive system of a self-ligating bracket with variable resistance to sliding presented herein, for every 0.01 mm that such deflection control components are advanced in the mesial distal direction in the body of the bracket, an increase of 50-100 grams of force occurs to deflect the blade or the clip vertically or perpendicular to the sliding channel. This result directly influences the rotational control of the tooth, due to the interaction of the blade or clip with the archwire.

In the constructive system of a self-ligating bracket with variable resistance to sliding presented herein, aspects may be applied in brackets, such as with internal or external sliding channels built in the tie wings.

In accordance with aspects of the constructive system of a self-ligating bracket with variable resistance to sliding presented herein, the bracket may be shut via use of a planar sliding blade or clip, and also via blades or clips in the shape of a "C", "U" or "J" that are manufactured with materials with mechanical shape memory alloy and reduced thickness.

In accordance with aspects of the constructive system of a self-ligating bracket with variable resistance to sliding presented herein, independent of blade or clip geometry, interaction and uniformity of forces in the bracket/archwire interface may be improved.

In accordance with aspects of the constructive system of a self-ligating bracket with variable resistance to sliding presented herein, the flexibility of the material with elastic memory utilized in the manufacturing of the blade or clip allows the interaction of the deflection of the archwire with the deflection of the blade or clip, partially absorbing the forces produced thereby. This effect promotes better control during the initial phases of the treatment.

Additional advantages and novel features of these aspects will be set forth in part in the description that follows, and in part will become more apparent to those skilled in the art upon examination of the following or upon learning by practice of the invention.

BRIEF DESCRIPTION OF THE DRAWINGS

Following, the invention will be explained with reference to the attached illustrations, presented in illustrative form and not limited thereto.

DETAILED DESCRIPTION

Figure 1:
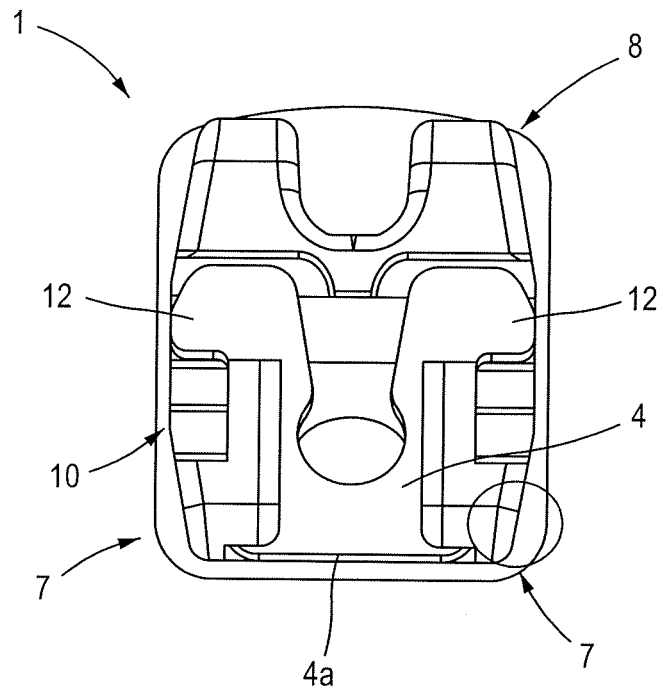
FIG. 1: Illustrates a schematic plan view of a bracket obtained with aspects of the present constructive system with the blade or clip in a closed position, showing example deflection control components in an advanced, intermediate and retracted position in relation to the archwire slot.

Aspects of an example constructive system 1 comprising a self-ligating bracket with variable resistance to sliding, as shown and described with regard to FIGS. 1-7, include features based on the structural alteration of the body of a bracket 3 that enable certain example deflection control components 10 and 7a (components 7a also interchangeably referred to herein as "locking elements") to be configured to be capable of adjusting the flexibility of the blades or clips 4 via action over the archwire 5 and allow adjustment of the resistance to sliding of various features in relation to the archwire slot 6.

Figure 2:
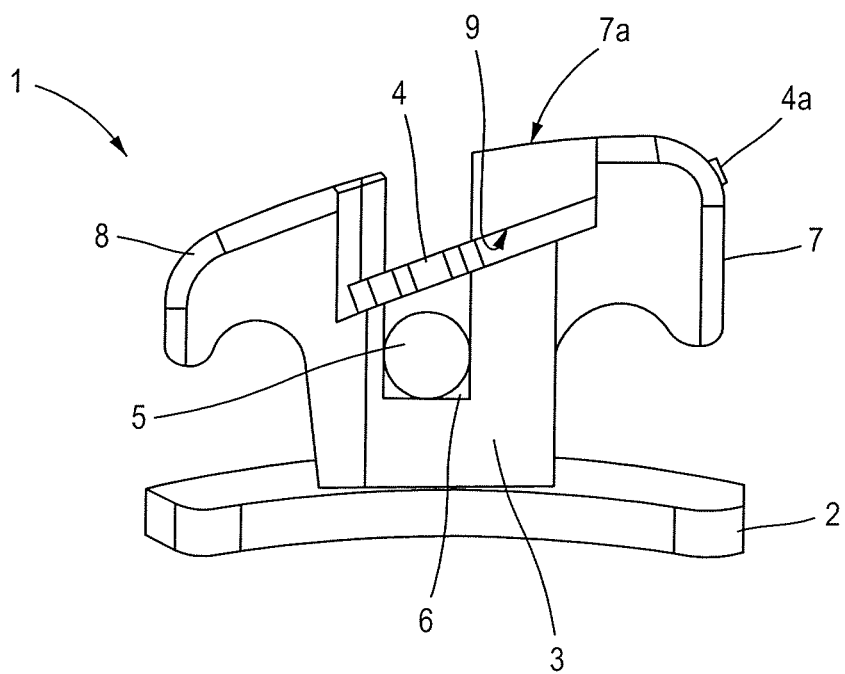
FIG. 2: Illustrates a plan view of the lateral profile of the bracket obtained with the blade or clip in a closed position, with example deflection control components shown in an advanced position.

More specifically, the example system shown in several variations in FIGS. 1-7 provides a self ligating bracket that includes a bonding base 2 with variable geometry (e.g., in its shape and size and with regard to its surface opposite the features for holding the archwire 5, e.g., the lower surface of base 2 as shown in FIG. 2) to match the surface anatomy of the tooth and a bracket body 3, subject to structural variations, to allow limiting or broadening of the field of movement of the blade or clip 4 that secures the archwire 5 in the archwire slot 6. A first set of tie wings 7 include first set of locking elements 7a for the blade or clip 4, when in a closed position (e.g., interaction of locking elements 7a cooperating in part with the blade or clip 4 enabling securing of an archwire 5 in archwire slot 6, as shown in FIG. 2), while a second set of tie wings 8 further cooperates to secure the blade or clip 4 in the sliding channels 9. Blade or clip 4 may include an extending portion 4a. Thus, first and second sets of locking elements and tie wings 7, 8 cooperate to secure blade or clip 4 at both mesial and distal ends thereof, so as to provide securing of the blade or clip 4 relative to the archwire slot 6. Bracket body 3 may also include bonding guide 15 to align the bracket during the procedure bonding the bracket to the tooth. For example, the bonding guide 15 may separate the mesial and distal housings for the clip 4.

Figure 3:
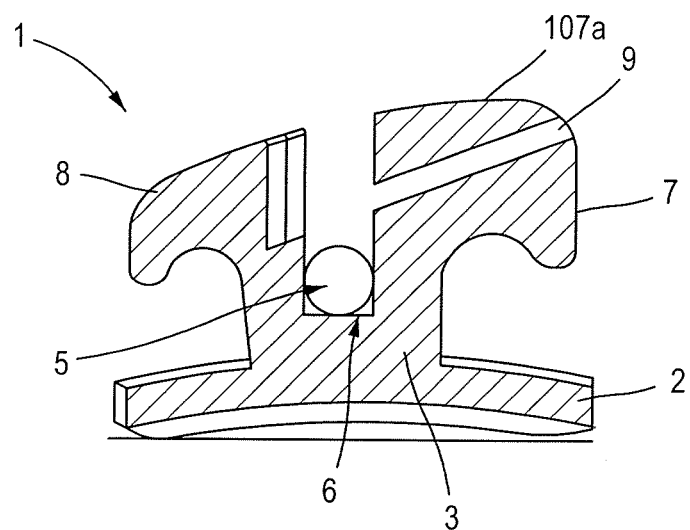
FIG. 3: Illustrates a cross-sectional view of the bracket obtained with aspects of the present constructive system without the blade or clip, with example deflection control components shown in an advanced position.
Figure 4:
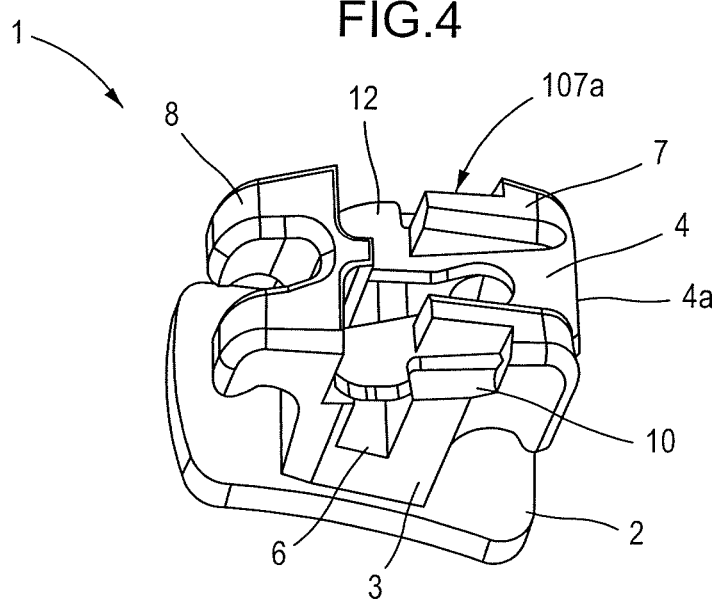
FIG. 4: Illustrates a perspective view of the bracket obtained with aspects of the present constructive system with the blade or clip in a closed position, showing the use of example deflection control components in an advanced position.

As further shown in FIGS. 3 and 4, by varying additional securing features for the blade or clip 4 relative to the first and second set of tie wings 7, 8, it is possible to make longitudinal or transversal adjustments of the blade or clip 4. Such longitudinal or transversal adjustments may be made, for example, by altering the adjustment of deflection control component 10 relative to the bracket body 3, particularly with regard to certain curve dimensions in deflection control component 10. These curve dimensions of such deflection control component 10 may be proportionally varied as appropriate for the flexibility of the blade or clip 4. In one variation, the combination of the dimension of curvature of certain aspects of deflection control component 10, along with the location of such curvature (e.g., proximity to the archwire slot 6), may be adjusted as appropriate for the amount of force exerted by the blade or clip 4 over the archwire 5 to thereby be appropriate for the amount of deflection of the blade or clip 4, so as to selectively restrict the movement of the archwire 5 inside the archwire slot 6.

As further shown in the variation of FIGS. 3-4, deflection control component 10 may include both a height adding feature, relative to bracket body 3, and/or curvature features (e.g., curvature partially extending toward and/or over the archwire slot 6, as shown in FIG. 4), so as to allow exertion of increased vertical force over the blade or clip 4 (e.g., via pressure exerted using locking elements 107a), and thus curvature of the blade or clip 4, relative to that exerted by the locking elements 7a in the variation shown in FIGS. 1 and 2, while maintaining restriction on the movement of the blade or clip 4. Optionally, further variation in these features may allow resistance to sliding of the archwire 5 within the archwire slot 6 to be varied.

Figure 5:
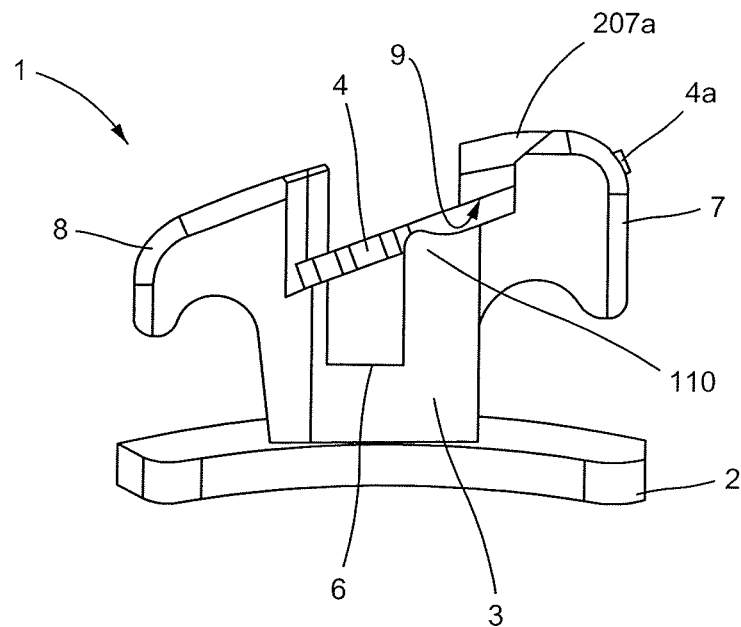
FIG. 5: Illustrates a lateral plan view of the bracket obtained with aspects of the present constructive system with the blade or clip in a closed position, with example deflection control components shown in an intermediate position.
Figure 6:
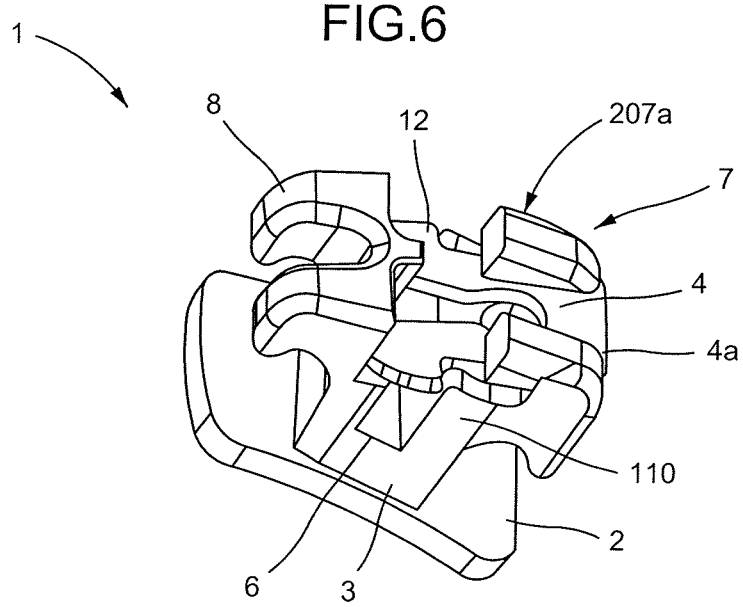
FIG. 6: Illustrates a perspective view of the bracket obtained with aspects of the present constructive system with the blade or clip in a closed position, showing example deflection control components in an intermediate position.
Figure 7:
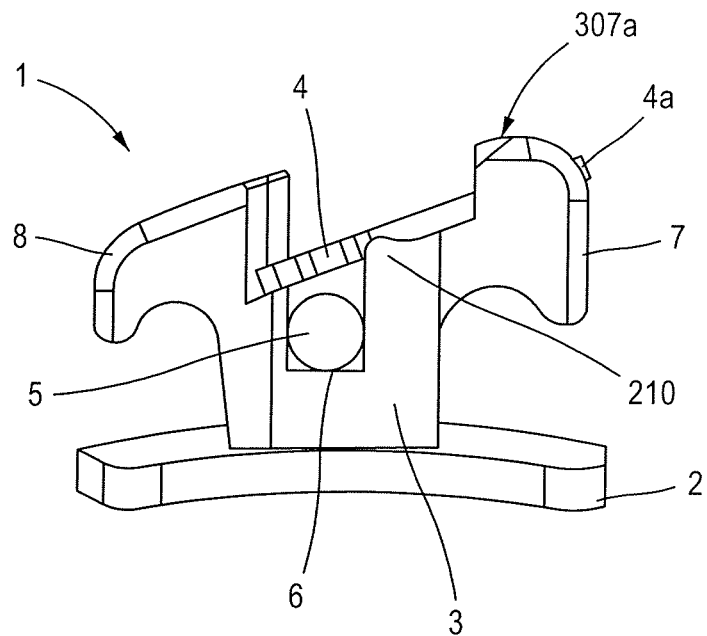
FIG. 7: Illustrates a lateral view of the bracket obtained with aspects of the present constructive system with the blade or clip in a closed position, with example deflection control components shown in a retracted position.
Figure 8:
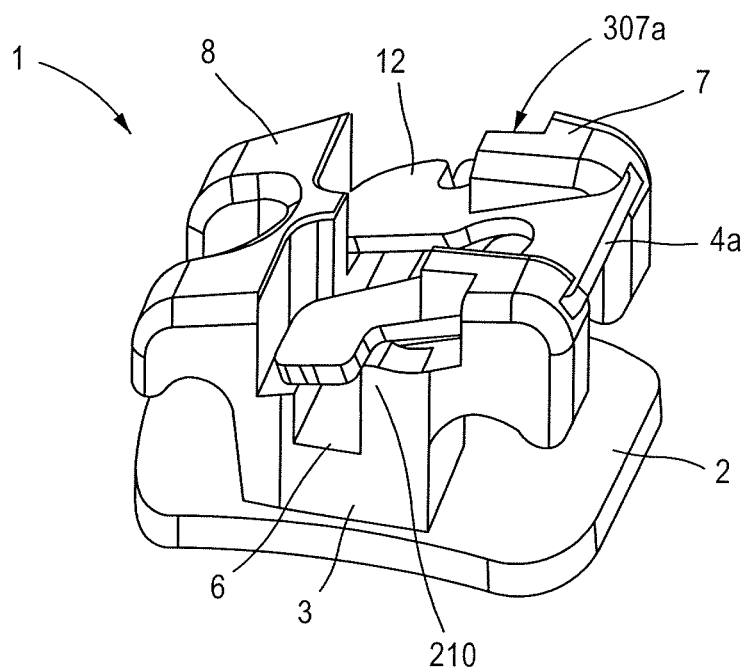
FIG. 8: Illustrates a perspective view of the bracket obtained with aspects of the present constructive system with the blade or clip in a closed position, showing example use with example deflection control components in an intermediate position.

The intermediate channel 9, according to aspects illustrated in FIGS. 5-6, which extends (e.g., via locking elements 207a) only partially to the opening in archwire slot 6, allows a medium resistance to the deflection of the archwire 5 to be provided, while an even less extending channel 9, via locking elements 207a, offers an even lower resistance to the deflection of the archwire 5, according to aspects illustrated in FIGS. 7-8.

The transversal deflection control components 110, 210 (as shown in FIGS. 5-6 and FIGS. 7-8, respectively) in the mesial-distal direction, also influence the flexibility of the blade or clip by enhancing resistance to displacement of the archwire 5, and thereby directly influencing the rotational control of the tooth to which the system 1 is attached.

The system 1 is applied with blades or clips 4, having generally a planar direction of extension, with a "C", "U" or "J" cross-sectional shape, or other suitable geometric configuration, which cooperate with the round, rectangular or square cross-sectional shaped archwires 5, to promote a uniformity of the forces generated in the bracket/archwire interface, as further described herein, through an alteration of the constructive structure of the system 1 that varies the resistance to sliding.

Functionally, for example, the arms 12 of the blade or clip 4 may allow the locking of the blade or clip 4 in the first set of tie wings 7 once the locking elements 7a located on the perpendicular wall of the tie wings 7 adjoining the bottom of the archwire slot 6 are emplaced, the arms 12 of the blade or clip 4 thereby covering the archwire slot 6 and maintaining the archwire 5 securely therebeneath. The flexibility of the material of which the blade or clip 4 is manufactured, such as to provide elastic memory to the blade or clip 4, allows interaction between the archwire 5 deflection and deflection of the arms 12.

The force generated by deflection of the archwire 5 may in part be absorbed by the deflection of the arms 12, which may thereby extend the range of action of the archwire 5. The force generated by the arms 12 and by their lateral extension may vary, depending on the extension of locking elements 107a, 207a, 307a (FIGS. 3-4, 5-6, 7-8, respectively). Thus functionally, the bracket body 3 to which the locking elements 107a, 207a, 307a (FIGS. 3-4, 5-6, 7-8, respectively) are secured, enables stability to the arm extensions 12 in cases where the archwire 5 are highly deflected, thereby keeping the archwire 5 confined to the archwire slot 6.

Figure 9:
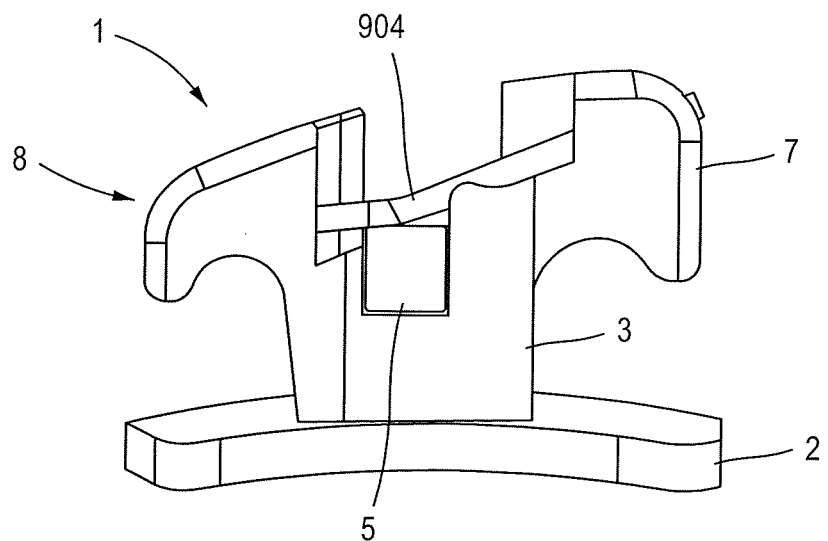
FIG. 9: Illustrates a lateral plan view of the bracket obtained with aspects of the present constructive system, with another geometric configuration for the blade or clip at the extremity shown.

The force of the archwire 5 that is absorbed may also be further affected by the shape of the arms of the clip and the arrangement thereof relative to the upper and lower tie wings. For example, in FIG. 9, the arms of the clip 904 may be angled and secured so as to abut a lateral wall of the lower tie wing 8, so as to provide further resistance to deflection by the force of the archwire 5.

Figure 10:
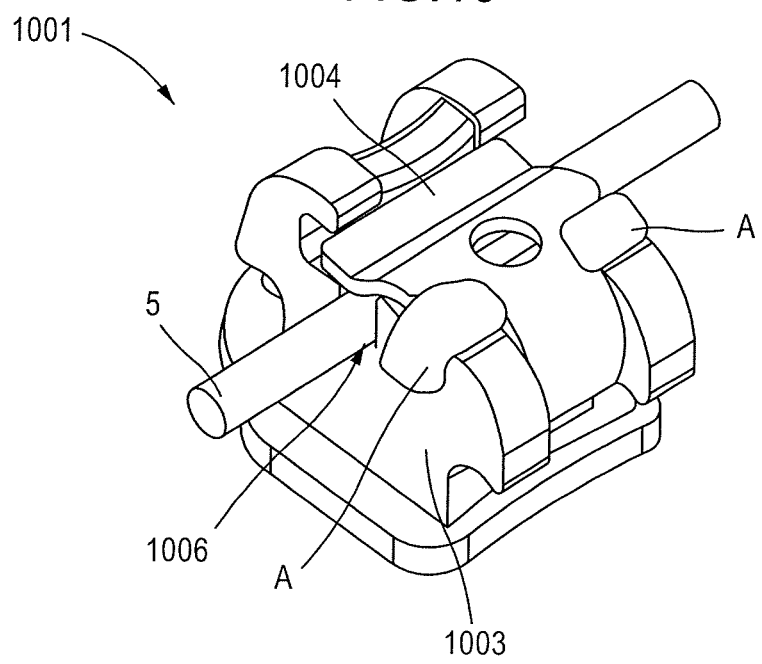
FIG. 10: Illustrates a perspective view of the bracket obtained with aspects of the present constructive system, in a first constructive variation with example deflection control components represented by supplements in "L" shaped forms.
Figure 11:
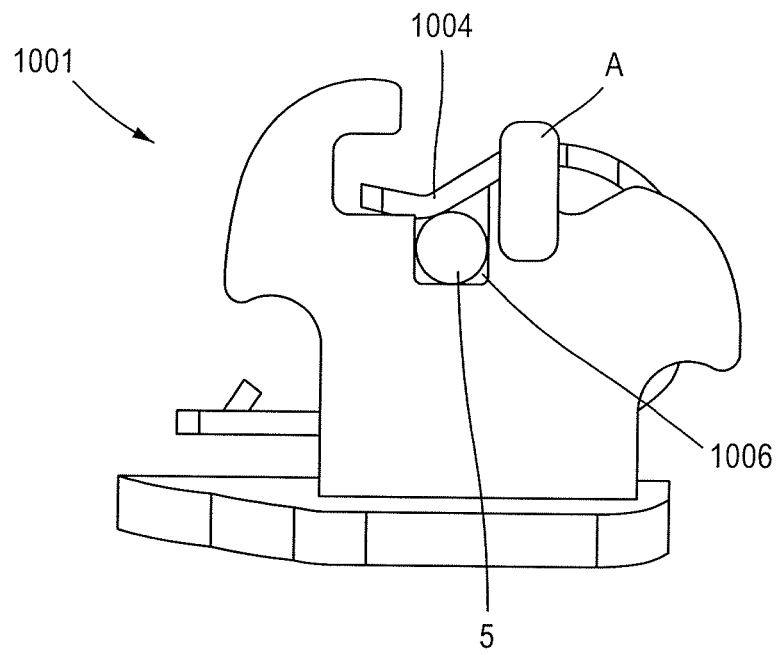
FIG. 11: Illustrates a lateral plan view of the bracket obtained with aspects of the present constructive system, in a first constructive variation with example deflection control components represented by supplements in an "L" shaped form, shown in an advanced position.
Figure 12:
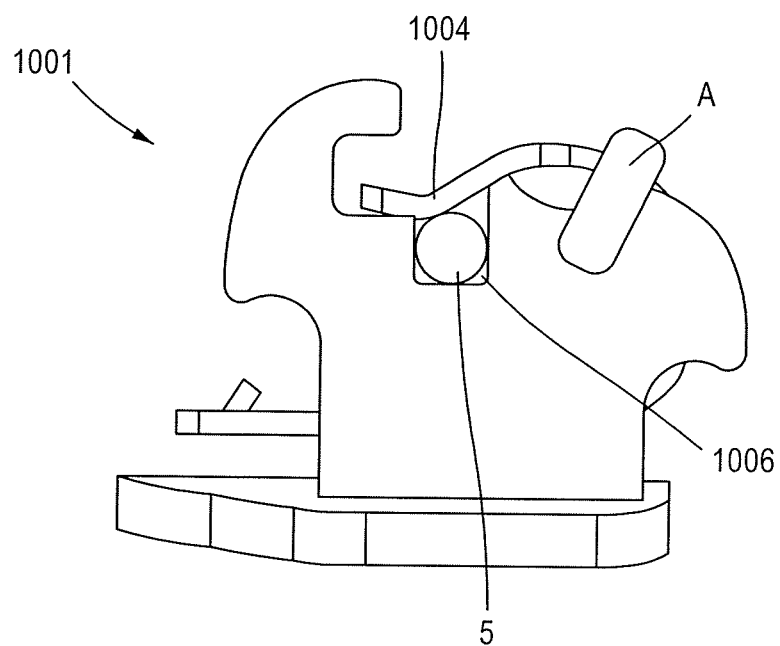
FIG. 12: Illustrates a lateral plan view of the bracket obtained with aspects of the present constructive system, in a first constructive variation with example deflection control components represented by supplements in an "L" shaped form, shown in an intermediate position.

In another example variation, according to FIGS. 10-12, the bracket body 1003 of an example system 1001 may have attached transversal mesial and distal deflection control components represented by supplements in an "L-shaped" form, illustrated as A in FIGS. 10-12, that actuate over blades or clips 1004 having a "J", "U" or "C" shape. Therefore, according to the position of the transversal deflection control component A, such as the "L-shaped" supplement, it is possible to modify the flexibility of the blade or clip 1004.

FIG. 11 shows a supplement in an "L" form A, more advanced with respect to being located toward the archwire slot 1006 (relative to the position of form A toward the slot 1006 as shown in FIG. 10), being so placed in order to exert an increased vertical force over the blade or clip 1004, that in return allows increased resistance to sliding of the archwire 5.

In FIG. 12, the "L-shaped" supplement A is in an intermediate position at a further distance from the archwire slot 1006 than in FIG. 11, thereby allowing a medium resistance to sliding of the archwire 5.

Figure 13:
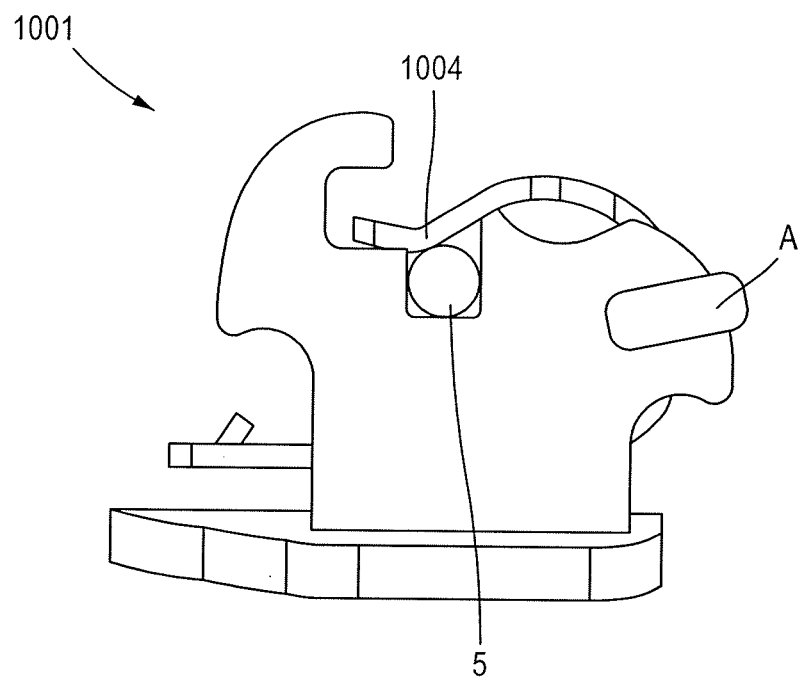
FIG. 13: Illustrates a lateral plan view of the bracket obtained with aspects of the present constructive system, in a first constructive variation with example deflection control components represented by supplements in an "L" shaped form, shown in a retracted position.

In FIG. 13, the "L-shaped" supplement A is retracted thereby offering lower resistance to archwire 5 displacement.

Figure 14:
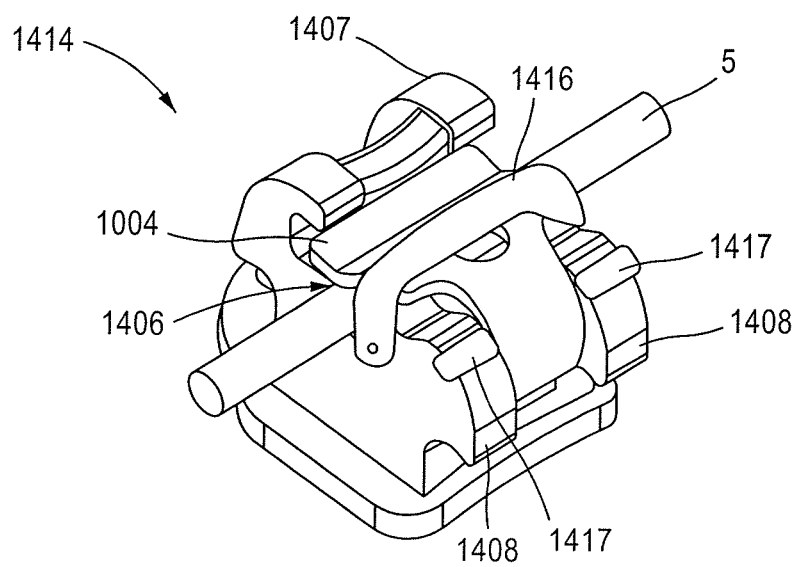
FIG. 14: Illustrates a perspective view of the bracket obtained with aspects of the present constructive system, in a second constructive variation with certain example lateral deflection control components represented by a mesio-distal movable bar.

In another example variation, aspects of which are presented in FIG. 14, the lateral deflection control component of the system 1414 is represented by a movable mesial-distal bar 1416 that is positioned approximately parallel to the archwire slot 1406. Displacement perpendicular to the archwire slot 1406, or in the gingival occlusal direction, of the bar 1416 allows adjustment of the flexibility extension of the blade or clip 1004 and thereby influences the resistance to sliding in the slot/archwire interface. Concave recesses 1417 in the second set of tie wings 1408 may be used to lock the bar 1416.

Figure 15:
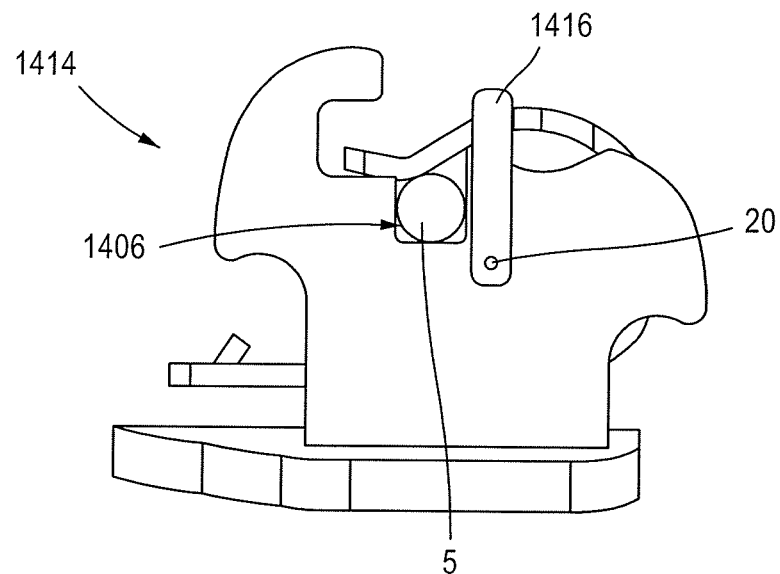
FIG. 15: Illustrates a lateral plan view of the bracket with aspects of the present constructive system, in a second constructive variation with certain example lateral deflection control components represented by a movable mesial-distal bar, shown in an advanced position.
Figure 16:
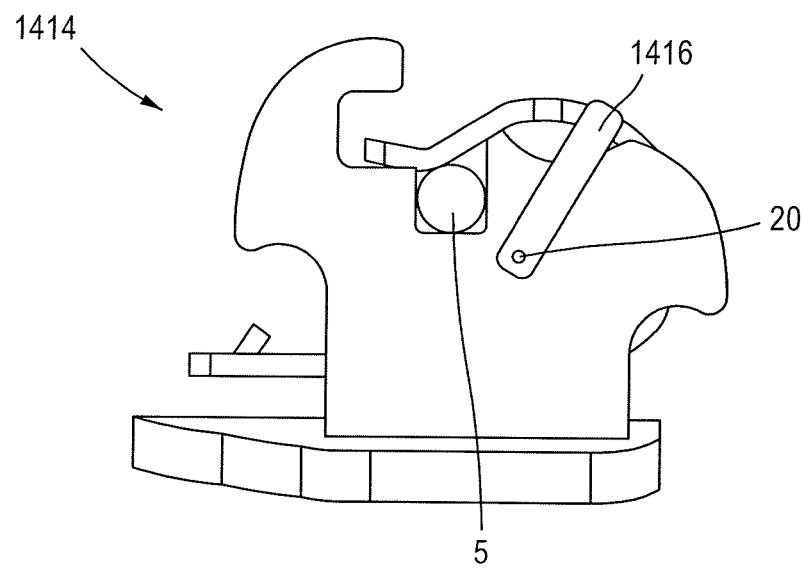
FIG. 16: Illustrates a lateral plan view of the bracket with aspects of the present constructive system, in a second constructive variation with certain example lateral deflection control components represented by a movable mesial-distal bar, shown in an intermediate position.
Figure 17:
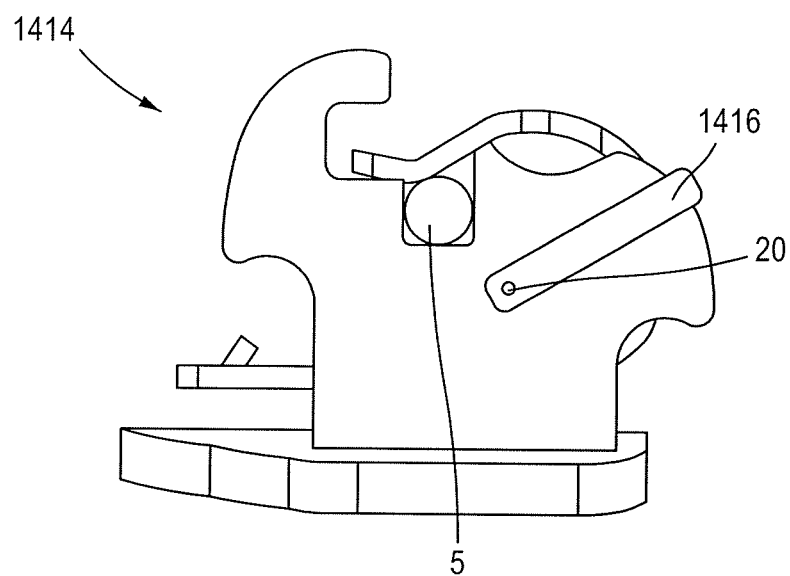
FIG. 17: Illustrates a lateral plan view of the bracket with aspects of the present constructive system, in a second constructive variation with certain example lateral deflection control components represented by a movable mesial-distal bar, shown in a retracted position.

FIG. 15 shows a side view of the movable mesial-distal bar 1416 of FIG. 14 located in a more advanced position (i.e., extension direction of the bar 1416 being generally toward the slot 1406, relative to FIG. 16, for example), thereby enabling the configuration to exert maximum resistance of the bar 1416 to sliding of the archwire 5. In FIG. 16, the movable mesial-distal bar 1416 is in an intermediate position, resulting in a medium resistance to sliding, while according to FIG. 17, the movable mesial-distal bar 1416 is retracted, thereby offering low resistance to sliding to the archwire 5 displacement.

Figure 18:
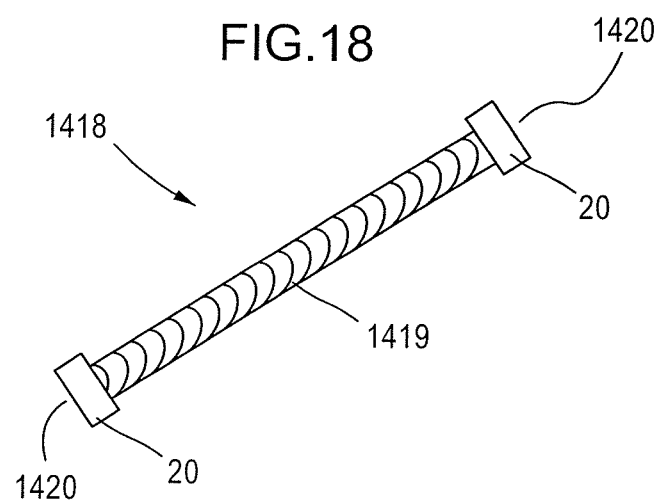
FIG. 18: Illustrates a detailed view of the telescopic rod with certain example laterally extending deflection control components shown, in accordance with aspects of the invented constructive system.

Structurally, as further shown in the representative drawing of FIG. 18, the movable mesial-distal bar 1416 (FIGS. 14-17) may be fixed to the body of the system 1407 (FIGS. 14-17) by a telescopic rod 1418 that includes, for example, a cylindrical tube portion and a round cross-sectional rod portion that is received within the interior of the cylindrical tube portion, with a helicoidal open spring 1419 therebetween, with the ends 1420 of the telescopic rod 1418 having two fixed elements 20.

Figure 19:
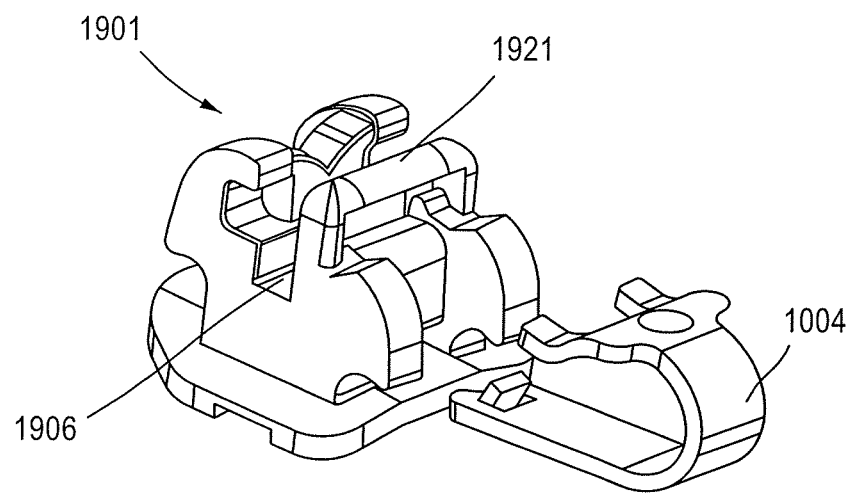
FIG. 19: Illustrates an exploded perspective view of the bracket obtained in accordance with aspects of the present constructive system, in an example constructive variation having certain example lateral deflection control components represented by a mesial-distal fixed bar.
Figure 20:
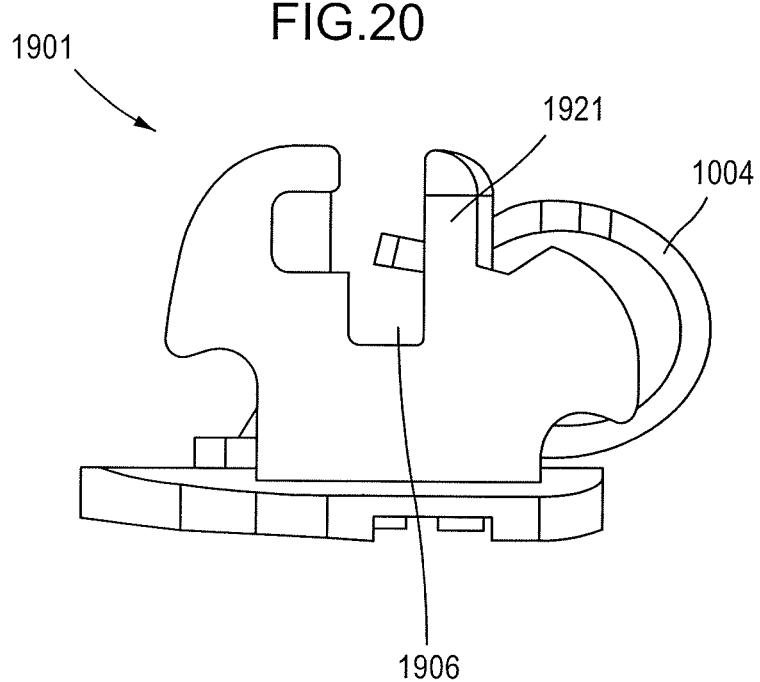
FIG. 20: Illustrates a lateral plan view of the bracket obtained with aspects of the present constructive system, with certain example lateral deflection control components represented by a mesial-distal bar fixed in an advanced position.

In yet another example variation of a system 1901, according to FIG. 19, the lateral deflection control component is represented by a fixed mesial-distal bar 1921 oriented approximately parallel to the depth direction of the archwire slot 1906. FIG. 20 shows a side view of the mesial-distal bar 1921 of FIG. 19, which, being located maximally advanced towards the archwire slot 1906, thereby allows maximum resistance to sliding of an archwire received in the slot 1906.

Figure 21:
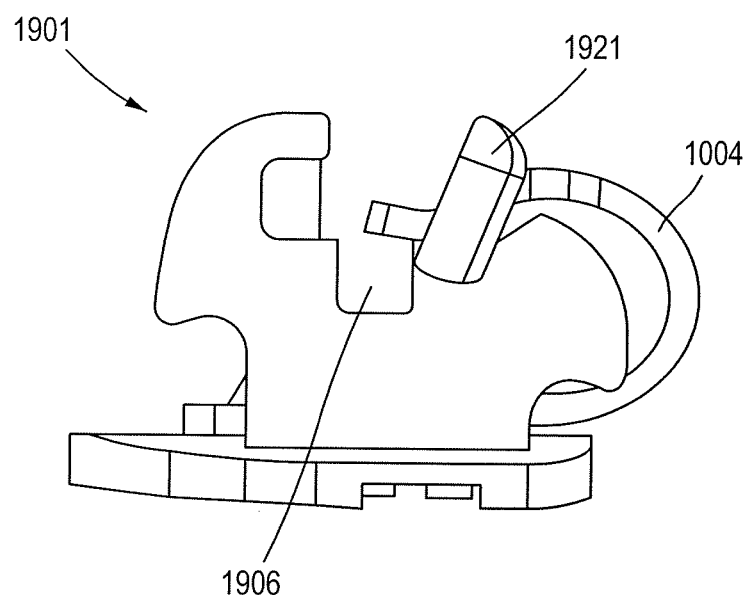
FIG. 21: Illustrates a lateral plan view of the bracket obtained with aspects of the present constructive system, with certain example lateral deflection control components represented by a mesial-distal bar fixed in an intermediate position.
Figure 22:
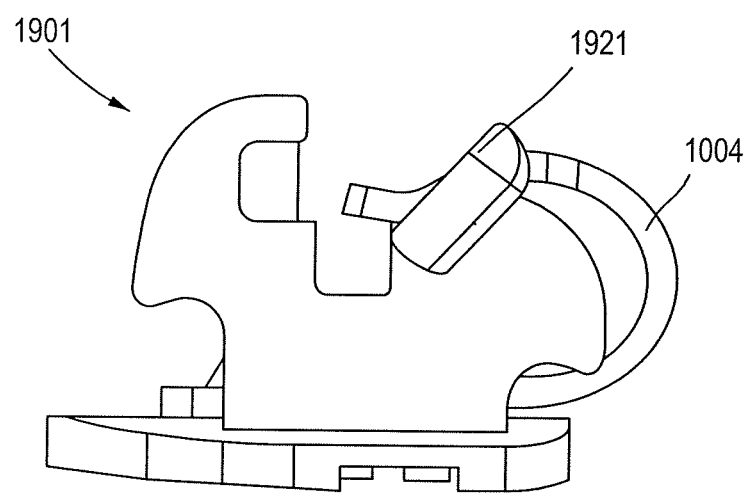
FIG. 22: Illustrates a lateral plan view of the bracket obtained with aspects of the present constructive system, with certain example lateral deflection control components represented by a mesial-distal bar fixed in a retracted position.
Figure 23:
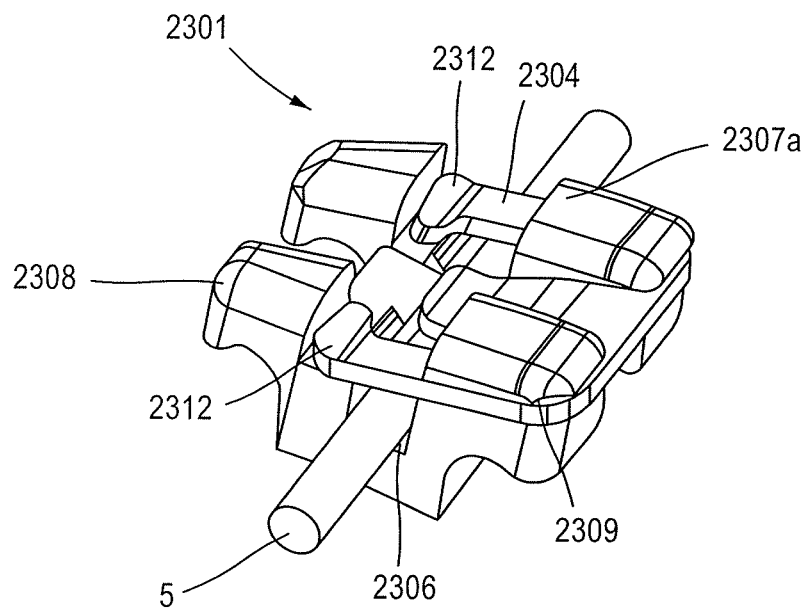
FIG. 23: Illustrates a perspective view of the bracket obtained with aspects of the present constructive system, with the external sliding channel and the blade or clip shown in a closed position.

In FIG. 21, the mesial-distal bar 1921 of FIGS. 20 and 21 is oriented in an intermediate position (e.g., an outer edge of the bar 1921 is oriented slightly away from the slot 1906, thereby resulting in a medium resistance to sliding of an archwire received in the slot 1906, while according to FIG. 22, the mesial-distal bar 1921 is retracted (oriented such that the outer edge of the bar 1921 is oriented maximally away from the slot 1906), thereby offering low resistance to sliding and displacement of an archwire received within the slot 1906.

Figure 24:
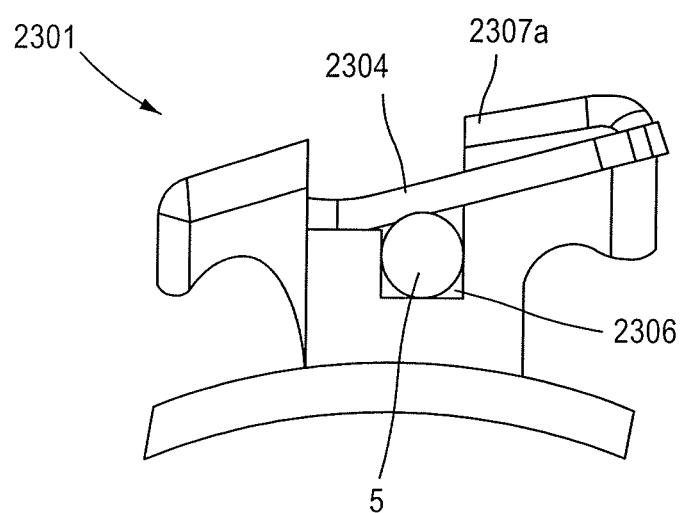
FIG. 24: Illustrates a lateral plan view of the bracket with the external sliding channel and the blade or clip in a closed position, with certain example deflection control components shown in an advanced position.

Similar features may be applied in the example constructive system 2301 shown in FIGS. 23-27, in which external sliding channels 2309 are located in the first set of tie wings 2308, which in a similar way to as shown in FIGS. 1-22, enables the extension of deflection control component 2307a to influence the resultant forces impacting the interface slot/archwire relation. Deflection control component 2307a is illustrated in a position more advanced towards the archwire slot 2306, as illustrated in FIG. 24. The deflection control component 2307a also is shown as approximately abutting the vertical wall of the housing of the slot 2306, thereby resulting in minimal free extension of the arms 2312 of the blade or clip 2304, thus restricting the displacement of the blade or clip 2304.

Figure 25:
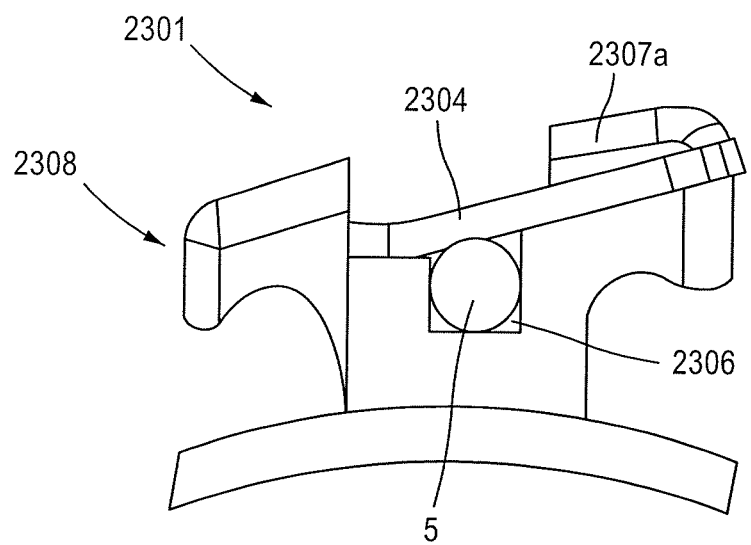
FIG. 25: Illustrates a lateral plan view of the bracket with the external sliding channel and the blade or clip in a closed position, with certain example deflection control components shown in an intermediate position.
Figure 26:
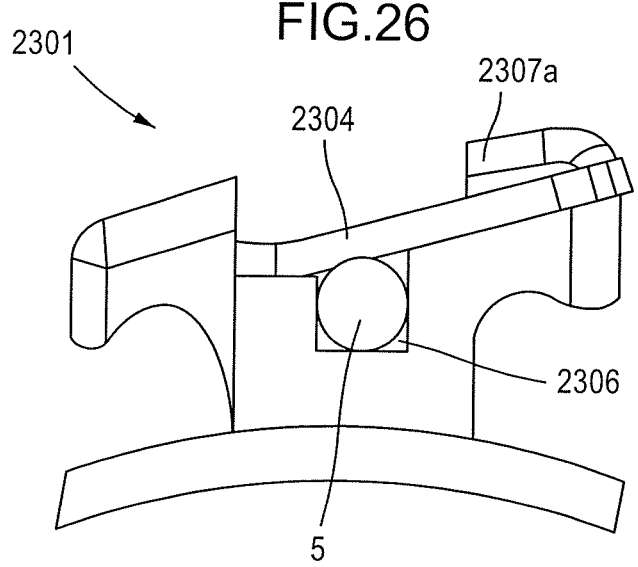
FIG. 26: Illustrates a lateral plan view of the bracket with the external sliding channel and the blade or clip in a closed position, with certain example deflection control components shown in a retracted position.
Figure 27:
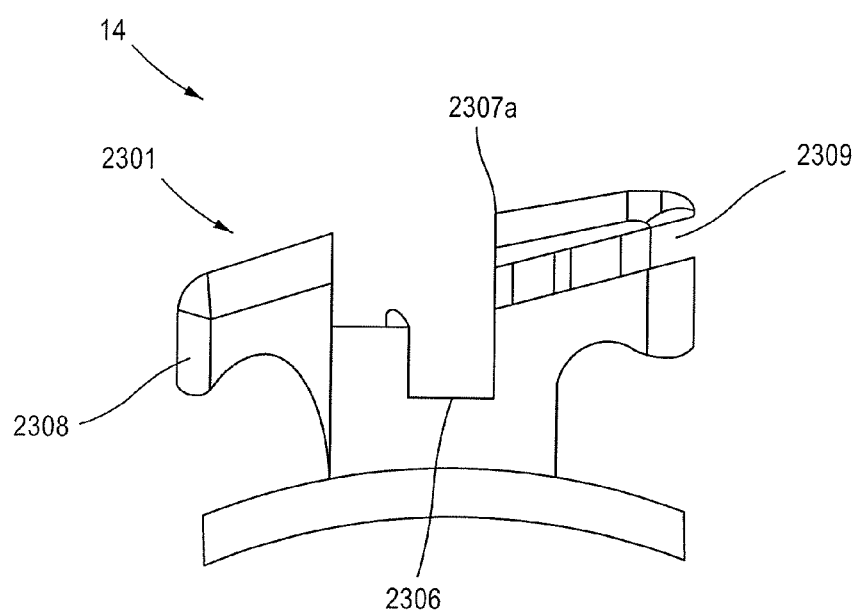
FIG. 27: Illustrates a lateral plan view of the bracket with the external sliding channel.

Intermediately restrictive deflection control component 2307a, according to FIG. 25, extending an intermediate distance toward the archwire slot 2306, as shown in FIG. 25, produces a medium resistance to archwire displacement 5 within slot 2306, while a more retracted deflection control component 2307a, as shown in FIG. 26, while not overly negatively impacting the stability of the opening and closing of the blade or clip 2304 for the application used, enables a wider free extension range of deflection of the arms 2312, than in the variations shown in FIGS. 24 and 25.

The constructive structure of the system 2301 of FIGS. 24-27 differs from the those of FIGS. 1-8, in part, by virtue of certain features of the arms 2312, which, whether in a planar version or being curved, are free to deflect in a direction generally perpendicular to the direction toward the bottom of the slot 2306. In addition, the arms 2312 allow deflection independently in the mesial-distal direction and dissipate excess forces produced by the deflection of archwire 5. These forces are transmitted to the blade or clip 2304, which is thereby elastically deformed. Accordingly, the sliding channels 2309 may be sized and shaped so as to allow movement of a received blade or clip 2304 in the buccal/lingual direction sufficient to allow lateral deflection of the blade or clip 2304.

In one example variation, the blade or clip 4, 904, 1004, 2304 comprises a memory shape alloy, such as a nickel/tin (Ni/Ti) alloy that may be capable, for example, of withstanding deformations within the elastic zone of the alloy with up to 10% strain recovery without plastically deforming.

While aspects of the present disclosure have been described in connection with preferred implementations, it will be understood by those skilled in the art that variations and modifications described above may be made without departing from the scope hereof. Other aspects will be apparent to those skilled in the art from a consideration of the specification or from a practice of the aspects of the invention disclosed herein.

What is claimed is:

1. A self-ligating bracket system having variable resistance to sliding, the system comprising:
   a bracket body, including an archwire slot formed therein for receiving an archwire;

at least a first tie wing attached to the body and having a clip receiving slot extending therein;

a clip retainably receiveable within the receiving slot of the at least a first tie wing, such that at least a portion of the clip extends over at least a portion of the archwire when the archwire is received in the archwire slot, the retainably received clip being configured to retain the received archwire; and a deflection control component configured to cooperate with the clip to securely retain the clip, wherein the deflection control component has a first end and a parallel section which has an axis parallel to the archwire slot, wherein the first end and the parallel section together form a substantially 90° angle, and wherein the first end of the deflection control component is fixed to the bracket body via at least a first point, such that the deflection control component is pivotable about the first point, thereby varying a position of the parallel section relative to the archwire slot and the clip, and wherein a flexibility of the clip to resist deflection to the archwire varies with a pivoted position of the deflection control component.

2. The system of claim 1, wherein the first end and the parallel section together form an L-shaped extension that extends from the bracket body upon attachment, to surround at least a portion of the clip.

3. The system of claim 1, wherein the deflection control component comprises a movable bar.

4. The system of claim 3, wherein the movable bar is attached to the at least a first tie wing via a telescopic rod having two fixed elements at its ends.

5. The system of claim 1, wherein the clip includes a pair of extending arms each extending over at least a portion of the archwire when the archwire is received in the archwire slot, wherein at least a portion of the pair of extending arms is curved.

6. A self-ligating bracket system comprising:

a body;

wherein the body includes at least a first wing and a through channel located proximal to the at least a first wing, the through channel being configured to receive an archwire;

an archwire-retaining clip;

wherein at least a portion of the archwire-retaining clip extends over at least a portion of the archwire when the archwire is received in the through channel such that the archwire-retaining clip retains the archwire with a force; and a clip-retaining element attached to the first wing, the clip-retaining element having a parallel section that extends over at least a portion of the archwire-retaining clip;

wherein the clip-retaining element has a first end that forms a substantially 90° angle together with the parallel section, and wherein the first end of the clip-retaining element is fixed to the body via at least one point, the clip-retaining element being pivotable about the at least one point thereby varying a position of the parallel section relative to the archwire-retaining clip, and wherein a flexibility of the archwire-retaining clip to resist deflection to the archwire varies with the position of the parallel section of the clip-retaining element relative to the archwire-retaining clip.

7. The system of claim 6, wherein the clip includes a pair of extending arms each extending over at least a portion of the archwire when the archwire is received in the archwire slot, wherein at least a portion of the pair of extending arms is curved.

* * * * *